(12) United States Patent
Shahrestani et al.

(10) Patent No.: US 12,303,274 B2
(45) Date of Patent: May 20, 2025

(54) COIL POSITIONING SYSTEM FOR NONINVASIVE BRAIN SENSOR

(71) Applicant: StrokeDx, Inc., Pasadena, CA (US)

(72) Inventors: Shane S. Shahrestani, Yorba Linda, CA (US); Alexander M. Ballatori, Rushville, NY (US); Brian L. Nguyen, Pasadena, CA (US); Robert Luke, St. Kilda West (AU); John M. Vernon, Malibu, CA (US); Lance G. Hussey, Simi Valley, CA (US); Cary R. Chow, Santa Monica, CA (US); Ravi K. Sawhney, Malibu, CA (US)

(73) Assignee: StrokeDx, Inc., Culver City, CA (US)

( * ) Notice: Subject to any disclaimer, the term of this patent is extended or adjusted under 35 U.S.C. 154(b) by 0 days.

(21) Appl. No.: 18/416,790

(22) Filed: Jan. 18, 2024

(65) Prior Publication Data
US 2024/0293063 A1 Sep. 5, 2024

Related U.S. Application Data

(60) Provisional application No. 63/588,278, filed on Oct. 5, 2023, provisional application No. 63/449,238, filed on Mar. 1, 2023.

(51) Int. Cl.
*A61B 5/00* (2006.01)
*A61B 5/245* (2021.01)

(52) U.S. Cl.
CPC ............ *A61B 5/245* (2021.01); *A61B 5/4064* (2013.01); *A61B 5/70* (2013.01); *A61B 5/721* (2013.01); *A61B 2562/12* (2013.01)

(58) Field of Classification Search
CPC ......... A61B 5/245; A61B 5/4064; A61B 5/70; A61B 5/721; A61B 2562/12
See application file for complete search history.

(56) References Cited

U.S. PATENT DOCUMENTS

| 4,979,519 A | 12/1990 | Chavarria et al. |
| 6,746,785 B1 | 6/2004 | Werner |

(Continued)

FOREIGN PATENT DOCUMENTS

| CN | 113133754 A | 7/2021 |

OTHER PUBLICATIONS

"How to Use Vscan to Measure Urinary Bladder", GE Healthcare, Available online at: https://www.youtube.com/watch?v=35Lda53ZuK0, Aug. 7, 2015, 3 pages.

(Continued)

*Primary Examiner* — Joel F Brutus
(74) *Attorney, Agent, or Firm* — Mark P. Mathison

(57) ABSTRACT

A helmet-like medical diagnostic apparatus that is fixed or worn has motorized gimbals that automatically swivel to positions around a patient's head. An end effector extends radially from the gimbals toward the head to place a coil or other directional sensor snugly against the scalp. A coil sensor can be part of a sensitive circuit to measure eddy currents within the brain. Accelerometers, or other tilt-measuring gauges, are compared between those on the sensor and those on the apparatus's base to determine the precise 3D orientation of the sensor when resting against the head. The orientation can compensate coil measurements, find an exact spot again, or map opposing sides of the patient's cranium, even with a fidgeting unconscious patient. The head can be scanned in its entirety, or a spot scan may be prompted from other diagnostic data.

20 Claims, 13 Drawing Sheets

(56) References Cited

U.S. PATENT DOCUMENTS

| | | | |
|---|---|---|---|
| 8,801,646 | B2 | 8/2014 | Han et al. |
| 11,475,987 | B2 | 10/2022 | Tai et al. |
| 2008/0230538 | A1 | 9/2008 | Brune |
| 2009/0112115 | A1 | 4/2009 | Huang et al. |
| 2011/0193575 | A1 | 8/2011 | Rubinsky et al. |
| 2011/0245707 | A1 | 10/2011 | Castle et al. |
| 2013/0123585 | A1 | 5/2013 | Kang |
| 2014/0358016 | A1 | 12/2014 | Shapira et al. |
| 2015/0339421 | A1 | 11/2015 | Srinivasan et al. |
| 2016/0007879 | A1 | 1/2016 | Gonzalez et al. |
| 2016/0007978 | A1 | 1/2016 | Gonzalez et al. |
| 2016/0343497 | A1 | 11/2016 | Clark et al. |
| 2017/0296838 | A1 | 10/2017 | Asahina et al. |
| 2017/0319099 | A1 | 11/2017 | Levinson et al. |
| 2018/0064364 | A1 | 3/2018 | Oziel et al. |
| 2018/0230538 | A1 | 8/2018 | Stamova-Kiossepacheva et al. |
| 2018/0239430 | A1 | 8/2018 | Tadi et al. |
| 2019/0111274 | A1 | 4/2019 | Saitoh et al. |
| 2020/0082926 | A1 | 3/2020 | Tai et al. |
| 2021/0251546 | A1 | 8/2021 | Tai et al. |

OTHER PUBLICATIONS

"LDC1612, LDC1614 Multi-Channel 28-Bit Inductance to Digital Converter (LDC) for Inductive Sensing", Texas Instruments, Available online at: http://www.ti.com/lit/ds/symlink/ldc1612.pdf, Mar. 2018, 67 pages.

Beynon, "A Glimmer of Hope for a Devastating Complication", Blood, vol. 129, No. 22, Jun. 1, 2017, pp. 2952-2953.

Gabriel et al., "Electrical Conductivity of Tissue at Frequencies Below 1 Mhz", Physics in Medicine and Biology, vol. 54, 2009, pp. 4863-4878.

Garcia-Martin et al., "Non-Destructive Techniques Based on Eddy Current Testing", Sensors, vol. 11, No. 3, 2011, pp. 2525-2565.

Giovangrandi et al., "Ballistocardiography—A Method Worth Revisiting", Conference Proceedings, IEEE Engineering in Medicine and Biology Society, Aug. 2011, pp. 4279-4282.

Grieten, "FibriCheck Beat-to-Beat Accuracy Compared with Wearable ECG in Broad Dynamic Range", Available online at: https://www.fibricheck.com/fibricheck-beat-to-beat-accuracy-compared-with-wearable-ecg-in-broad-dynamic-range/12, Jun. 20, 2019, 17 pages.

Lin, "Radiation Risk from Medical Imaging", Mayo Clin. Proc., vol. 85, No. 12, Dec. 2010, pp. 1142-1146.

Nabavi et al., "Design Strategies for Eddy-Current Displacement Sensor Systems: Review and Recommendations", IEEE Sensors Journal, vol. 12, No. 12, Dec. 2012, pp. 3346-3355.

Oberhauser, "Optimizing L Measurement Resolution for the LDC161X and LDC1101", Texas Instruments, Available online at: http://www.ti.com/lit/an/snoa944/snoa944.pdf, Feb. 2016, 9 pages.

Robertson et al., "Clinical Evaluation of a Portable Near-Infrared Device for Detection of Traumatic Intracranial Hematomas", Journal of Neurotrauma, vol. 27, No. 9, Sep. 2010, pp. 1597-1604.

Ramrakhyan et al., "Design and Optimization of Resonance-Based Efficient Wireless Power Delivery Systems for Biomedical Implants", IEEE Transactions on Biomedical Circuits and Systems, vol. 5, No. 1, Feb. 2011.

PCT/US2024/012062 "International Preliminary Report on Patentability (Chapter II of the Patent Cooperation Treaty)" [IPRP], Oct. 2, 2024, 15 pages, European Patent Office as International Preliminary Examination Authority, Rijswijk, Netherlands.

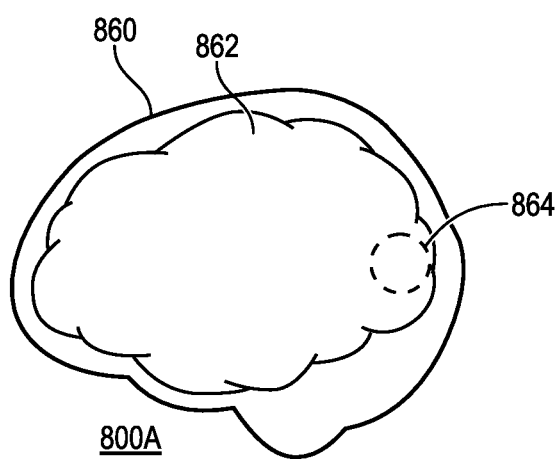 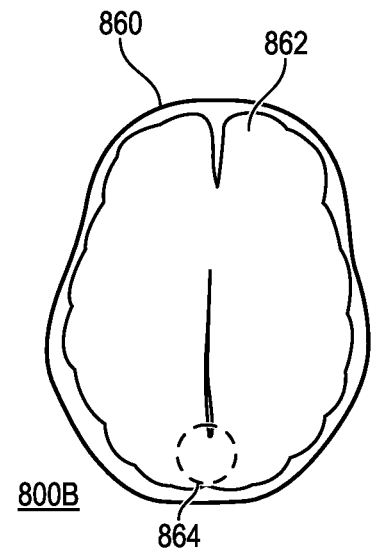
FIG. 8A  FIG. 8B
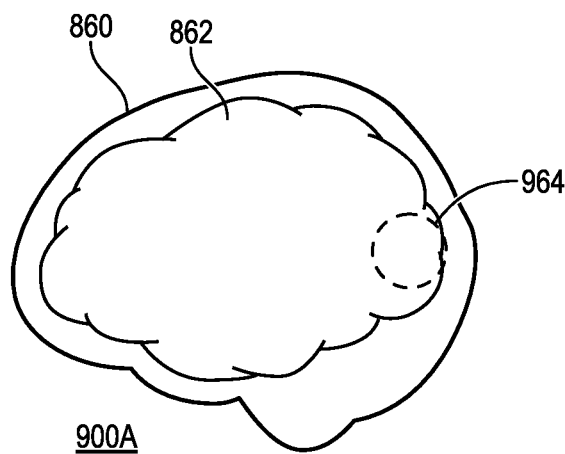 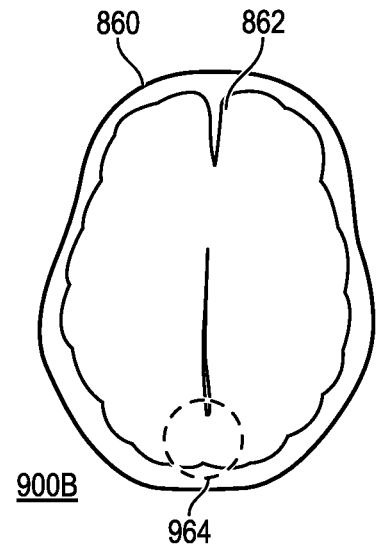
FIG. 9A  FIG. 9B

COIL POSITIONING SYSTEM FOR NONINVASIVE BRAIN SENSOR

CROSS-REFERENCES TO RELATED APPLICATIONS

This application claims the benefit of U.S. Provisional Application No. 63/449,238, filed Mar. 1, 2023, and U.S. Provisional Application No. 63/588,278, filed Oct. 5, 2023, the contents of which are hereby incorporated by reference in their entireties for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Art

Embodiments of the present invention generally relate to arrangements of detecting and measuring, for diagnostic purposes, electromagnetic anomalies within a subject's head with specially adapted means to be attached thereto, including means for indicating the position of a sensor on the body. Specifically, they relate to robotically positioning and repositioning a coil or other directional sensor against the subject's scalp, detecting the sensor's precise anatomical position and orientation with respect to the head, and outputting calibrated measurements.

2. Description of the Related Art

Diagnosing a possible stroke in a patient is frequently difficult because the stroke victim is often unconscious, and there are few, if any, visible indications of what is going on inside the patient's cranium. Further, a treating physician is under time pressure to proceed with a course of treatment. Each minute that passes untreated—or with the wrong treatment—can result in greater and greater brain damage, often permanent.

The wrong treatment may be fatal. Treatment for an ischemic stroke involves administering blood thinners. However, if the patient is actually experiencing a hemorrhagic stroke, then the blood thinners may worsen the problem by letting internal bleeding within the brain continue unabated by the blood's natural coagulation properties.

Currently, computed tomography (CT) and magnetic resonance imaging (MRI) are the two gold standards for diagnosing and monitoring brain health for stroke patients. When available, they help immensely by providing a treating physician with a view inside the patient's brain. And they are employed repeatedly on the patient so as to track progress, or lack thereof.

However, these devices are large, expensive, often require specialized staff, and are mostly restricted to larger hospital systems. CT scans give a non-negligible radiation dose, which adds to the patient's cancer risk. Neither can be used continuously on a patient bedside.

There is a need in the art for portable and less expensive systems that can detect a fluidic anomaly within a patient's head and monitor it over time, among other things.

BRIEF SUMMARY

A medical diagnostic device for a patient's head includes a temporarily or permanently fixed headrest base with a gimbal assembly that can pivot to latitudes and longitudes over the patient's sphere-like skull. An end effector mounted on the gimbal assembly can robotically extend inward from the gimbal to place a coil or other directional sensor against the patient's scalp. The sensor may cant slightly when pressing against the scalp in order to conform to the scalp's local topology. A tilt sensor affixed to the coil sensor measures this cant with respect to the base, and the precise orientation and position of the coil sensor with respect to the headrest are then known for the coil's magneto-electrical measurement.

Precisely located measurements, such as eddy current measurements, can be compared over time or with respect to the left and right hemispheres of the brain. Computed tomography (CT) data or magnetic resonance imaging (MRI) data can be uploaded into the device to spot check Some embodiments of the present invention are related to an inductive sensor apparatus for brain diagnostics, the apparatus including a headrest plinth configured to hold a head of a subject, the subject's head having a notional spherical center point, a first tilt gauge rigidly attached to the plinth, a gimbal armature pivotably attached to the plinth and configured to pivot a mounting point on the gimbal armature to latitudes and longitudes around the center point, a radial extender mounted to the mounting point of the gimbal armature, the radial extender configured to extend an end effector inward along a radial line with respect to the center point, a coil sensor affixed to the end effector, and a second tilt gauge affixed to the sensor.

The apparatus can further include a memory and a computer processor operatively coupled with the machine-readable non-transitory medium embodying information indicative of instructions for causing the computer processor to perform operations comprising comparing tilt angles from the first tilt gauge and the second tilt gauge to determine a relative orientation of the coil sensor, and calculating a three-dimensional (3D) anatomical location of a measured value from the coil sensor based on the orientation.

The operations can further include adjusting a measured value from the sensor based on the orientation. The adjusting can include compensating for movement of the subject's head between measurements at the same anatomical location. The operations can further include commanding the gimbal to rotate to a specified latitude and a specified longitude, directing the radial extender to extend the sensor at the specified latitude and the specified longitude, generating a measured value based on output created by the sensor, and associating the measured value with the 3D anatomical location to create an anatomically located measurement. The anatomically located measurement can be from a left hemisphere of the brain/head, and the operations can further include making an anatomically located measurement on a right hemisphere of the brain/head, comparing the measurements from the left and right hemispheres of the head, and outputting an indication based on the comparing. The anatomically located measurement can be from an earlier time, and the operations can further include making an anatomically located measurement at a later time, comparing the measurements from the earlier and later times, and outputting an indication based on the comparing. The operations can further include accessing computed tomography (CT) data or magnetic resonance imaging (MRI) data from a scan of the head, and determining an anatomical coordinate in the head based on the CT or MRI data, wherein the specified latitude and specified longitude are based on the anatomical coordinate. The operations can further include creating a set of anatomically located measurements that includes the anatomically located measurement, and generating a physical topography of the head from the measurements or rendering an image based on the measurements. The apparatus can further include a resistive, inductive, and capacitive (RLC) circuit electrically connected with the coil sensor and a frequency counter electrically connected with the RLC circuit, and the operations can further include generating measured values based on outputs from the frequency counter when the coil sensor is at a cranial location on the head. The coil sensor can be a first coil sensor, the RLC circuit can be a first RLC circuit, and the frequency counter can be a first frequency counter, and the apparatus can further include a second coil sensor having a larger or smaller diameter than the first coil sensor, the first and second coil sensors sharing a housing, a second RLC circuit electrically connected with the second coil sensor, and a second frequency counter electrically connected with the second RLC circuit.

The first and second tilt gauges can include three-dimensional (3D) accelerometers. The radial extender can include a scissoring device or a telescoping mechanism. The apparatus can further include a motor, a pulley wheel on the mounting point, and a pulley cable extending between the motor and the radial extender through the pulley wheel, the motor located remotely from the mounting point in order to avoid electromagnetic interference with the coil sensor.

Some embodiments are related to a method of anatomically locating measurements in a subject's brain, the method including providing a headrest plinth configured to hold a head of a subject, the subject's head having a notional spherical center point, a first tilt gauge rigidly attached to the plinth, a gimbal armature pivotably attached to the plinth and configured to pivot a mounting point on the gimbal armature to latitudes and longitudes around the center point, a radial extender mounted to the mounting point of the gimbal armature, the radial extender configured to extend an end effector inward along a radial line with respect to the center point, a coil sensor affixed to the end effector, and a second tilt gauge affixed to the sensor, comparing tilt angles from the first tilt gauge and the second tilt gauge to determine a relative orientation of the sensor, and calculating a three-dimensional (3D) anatomical location of a measured value from the sensor based on the orientation.

The method can further include adjusting a measured value from the sensor based on the orientation. The method can further include commanding the gimbal to a specified latitude and a specified longitude, directing the radial extender to extend the sensor at the specified latitude and the specified longitude, generating a measured value based on output created by the sensor, and associating the measured value with the 3D anatomical location to create an anatomically located measurement. The anatomically located measurement can be from a left hemisphere of the brain/head, and the method can further include making an anatomically located measurement on a right hemisphere of the head, comparing the measurements from the left and right hemispheres of the head, and outputting an indication based on the comparing. The anatomically located measurement can be from an earlier time, and the method can further include making an anatomically located measurement at a later time, comparing the measurements from the earlier and later times, and outputting an indication based on the comparing.

Some embodiments are related to a method of manufacturing an inductive sensor apparatus for brain diagnostics, the method including providing a headrest plinth configured to hold a head of a subject, the subject's head having a notional spherical center point, rigidly attaching a first tilt gauge to the plinth, pivotably attaching a gimbal armature to the plinth so that the gimbal armature is configured to pivot a mounting point on the armature to latitudes and longitudes around the center point, mounting a radial extender to the mounting point of the gimbal armature so as to configure the radial extender to extend an end effector inward along a radial line with respect to the center point, affixing a coil sensor to the end effector, and affixing a second tilt gauge to the sensor.

The methods can include combinations of features of the apparatus, and the apparatus and methods may include some described aspects and not others in various combinations.

BRIEF DESCRIPTION OF THE DRAWINGS

FIG. 8A is a screen rendering of a lateral view of a patient's head and brain in accordance with an embodiment.

FIG. 8B is a screen rendering of a ventral view of a patient's head and brain in accordance with an embodiment.

FIG. 9A is a screen rendering of a lateral view of a patient's head and brain in accordance with an embodiment.

FIG. 9B is a screen rendering of a ventral view of a patient's head and brain in accordance with an embodiment.

DETAILED DESCRIPTION

Figure 1:
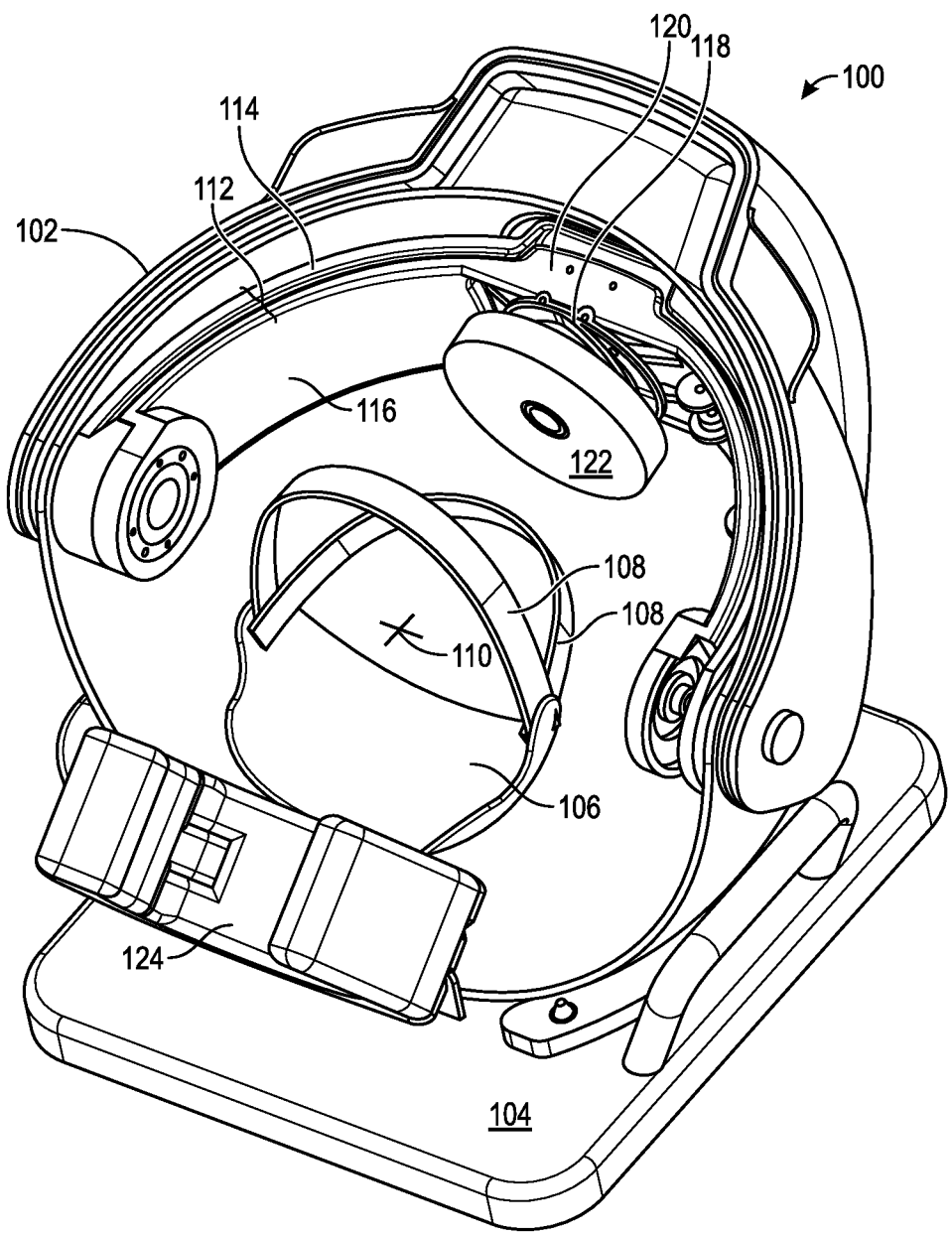
FIG. 1 is a perspective view of a medical diagnostic device in accordance with an embodiment.

A medical device for locating and orienting a coil-based or other type of directional sensor at positions around a patient's head is described. The positioning device can be small enough to be placed bedside or worn by the patient for point-of-care or continuous monitoring or diagnosis. Its sensor scans can, to some extent, substitute for those of a much larger computed tomography (CT) or magnetic resonance imaging (MRI) machine, and its size and low recurring cost allows more frequent use. It may also have utility in the realms of ambulatory care, rapid triage, the military, nursing facilities, sports, ambulances, and urgent care settings.

A coil sensor may use eddy current damping (ECD) to compare conductivity in various portions of the patient's brain, comparing them with respect to left and right hemispheres, over time, or with respect to other people's brains. In this application, "head" and "brain" are sometimes used interchangeably for areas of diagnostics.

Unlike traditional eddy current damping (ECD) sensors used in industry for metal crack inspection, which consist of a bridge circuit that measures the coil sensor impedance, some embodiments can have the coil sensor paired with a capacitor to form an electrical resonant circuit.

Automated eddy current-based technologies have a myriad of applications for assessing brain health. These devices can be used either continuously or intervally measure changes in brain fluid status, and they can be used in the settings of assessing ischemic or hemorrhagic strokes, brain tumors, hydrocephalus, arteriovenous malformations, congenital anomalies, traumatic brain injury, concussions, vascular neurosurgery, endovascular neurosurgery, neurodegenerative conditions (i.e., Alzheimer's Disease), and monitoring brain health when infusing drugs targeting the brain, among other brain-health related conditions.

Using information regarding conductivity shifts in the brain as brain fluid volumes change, such devices can provide information regarding the depth, location, size, volume, progression, type, and conductivity of the fluid change.

In addition, if a device is used in the operating suite, it may also be able to provide information about the location, size, and action of operative tools. This can be used either in endovascular neurosurgery (i.e., thrombectomies, coiling, etc.), cardiac surgery (i.e., throwing clots to the brain resulting in ischemic stroke), or general neurosurgery (i.e., assessing bleeding or implant placement).

Embodiments of the described device may have several design forms. The device may resemble a helmet and sit on the patient's head for point-of-care or continuous diagnosis or monitoring of brain-health conditions. Or, the automated device may be bedside and resemble a robotic arm or other fixture. In either case, the automated device may include a gimbal armature and motors that move a sensor in x-, y-, and/or z-planes, cylindrical, or spherical coordinates to capture one-dimensional (1D), two-dimensional (2D), or three-dimensional (3D) conductivity information about the brain. More particularly, aside from movements around a notional spherical center point in a patient's head, the device may be moved radially (i.e., closer or farther from the center point) to further obtain depth information regarding the object being tracked. Movement in the radial direction may also allow for varying spatial, temporal, and depth resolution.

Various other types of sensors may be introduced onto or alongside the inductive damping sensor, such as accelerometers, gyroscopes, piezoelectric sensors, or temperature sensors. The automated device may include encoders or precision stepper motors to package conductivity information with spatial information. These additional sensors and machines can be used to improve the overall accuracy or precision of the inductive damping sensor. For example, accelerometers and gyroscopes can allow for device positioning and trajectory mapping as the device is moved around the body, while temperature sensors can allow for temperature compensation to increase signal accuracy.

Data obtained by the device can be stored on a local, remote, cloud or cell network. Transmission of data may be through the use of a wire, BLUETOOTH® signal, radio frequency, or infrared. This can allow for the possibility of remote diagnostics based on patient data and also the possibility of directly reporting information into an electronic medical record (cMR). This would also allow for consolidation of data for analysis.

Following or during data collection, data may be displayed to a healthcare provider in several forms. The output may be shown on a local computer or tablet, or it may be stored on the eHR for later recall. Images of the conductivity distribution of the brain can be collected and shown in 2D or 3D figures. There may be a 'scrubbing' function, where the user can temporally pass through multiple images over a certain period of time. In addition, percentages and likelihoods of lesion presence or change may be displayed to the user.

FIG. 1 is a perspective view of an inductive sensor medical diagnostic device assembly 100 for brain diagnostics in accordance with an embodiment. Inductive sensor device 102 includes headrest plinth 104, upon which headrest 106 is attached.

Headrest 106 is curved and positioned such that it will cradle a human subject's head such that notional center point 110 of the subject's skull is somewhat centered within the larger apparatus in a positioning envelope for the head. Head straps 108 help secure a subject's head firmly to headrest 106. Neck cradle 124 can gently affix the patient's neck in place to minimize larger head movements and help keep the rest of the patient's body in place.

Affixed to headrest plinth 104 is gimbal armature 112, in this case an assembly of two gimbal arms: outer gimbal arm 114 and inner gimbal arm 116. Outer gimbal arm 114 is affixed to a raised portion of headrest plinth 104 and pivots around a notional axis that extends vertically through the top of a patient's head. The outer gimbal arm 114 can circle around a patient's head to different longitudes. Inner gimbal arm 116 is affixed by two pivots, each on opposite sides of the head, to outer gimbal arm 114. Pivoting up and down in relation to outer gimbal arm 114 and the patient's head, inner gimbal arm 116 can reach different latitudes on the patient's head. That is, inner gimbal arm 116 can rotate mounting point 120 up and down to different latitudes. Outer gimbal arm 114 rotates inner gimbal arm 116, and thus mounting point 120, to different longitudes. The assembly of gimbal armature 112, with outer gimbal arm 114 and inner gimbal arm 116, can thus pivot mounting point 120 to various latitudes and longitudes around notional center point 110.

Radial extender 118 is mounted to mounting point 120 of gimbal armature 112 and is oriented to extend inward. This particular radial extender extends its end effector along a radial line to notional center point 110.

Coil sensor 122 is mounted on the end effector of radial extender 118 such that coil sensor 122 moves along the radial line at the latitude and longitude stopped at by gimbal armature 112. When extended, the coil sensor can press up against a subject's head in order to be non-intrusively as close to the patient's brain as possible.

Several separate, different diameter coils may be nested inside one another to enable the depth mapping of readings within the head. Smaller coils typically measure less deeply than larger coils. In order to get a good signal to noise ratio with small coils, it can be important to get the small coils right up against the head, as close as possible to the subject's brain.

While coil sensors are shown within the various figures, other types of directional or omnidirectional sensors may also be used, including antenna, infrared, temperature, haptic, topographic, or others. Besides sensors, other end effectors can be used as well, such as robotic graspers, cranial drills, needles, and others.

Figure 2:
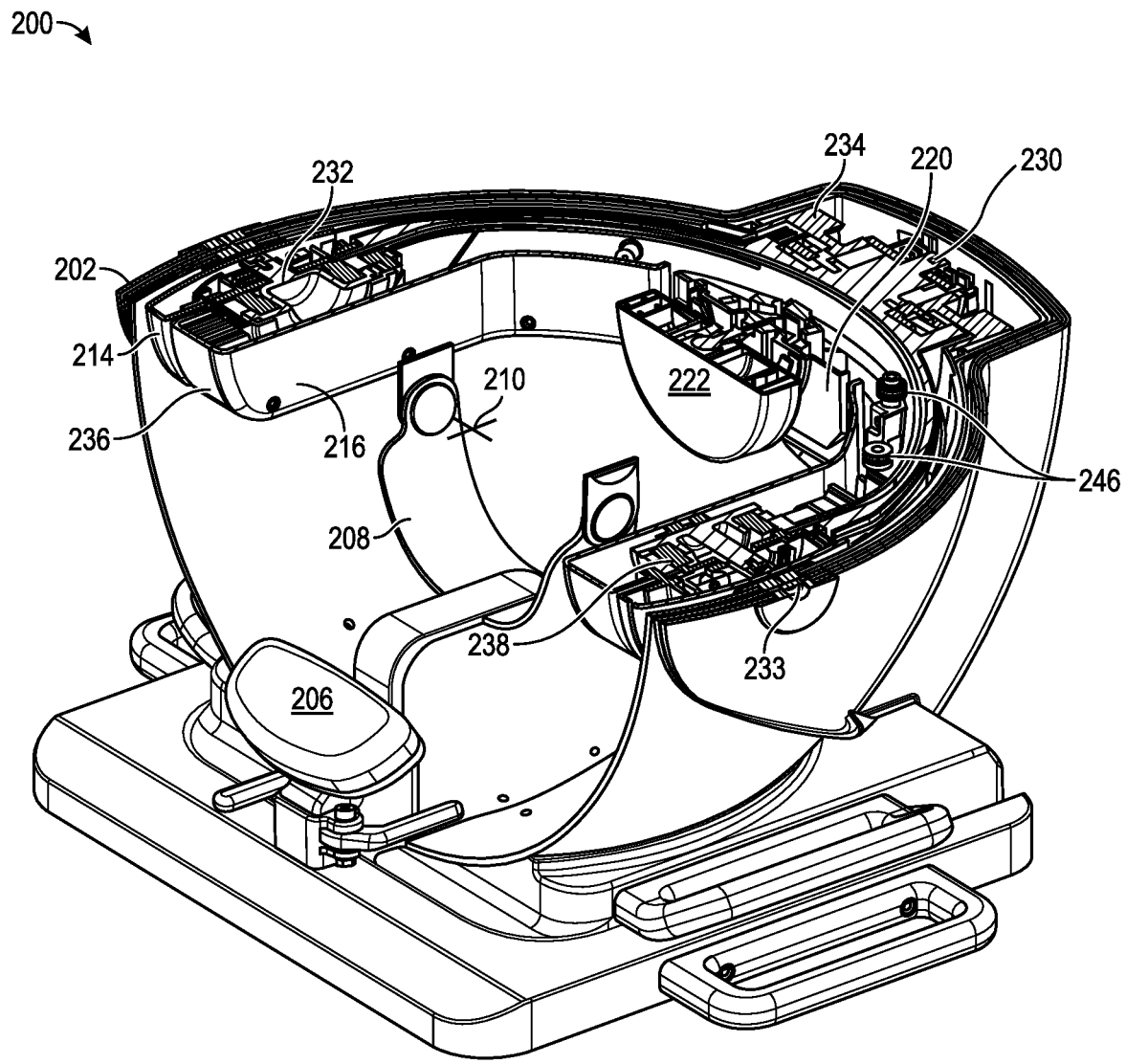
FIG. 2 is a horizontal cut-away view of a device in accordance with an embodiment.

FIG. 2 is a horizontal cut-away view of gimbaled device assembly 200 in accordance with an embodiment. Device 202 includes neck rest 206 supported by a headrest plinth as well as head strap 208 extending to left and right sides of a subject's head. Gimbal arms 214 and 216 pivot mounting point 220 at a constant radius around notional head center point 210, which is more or less at the center of the head strap. Sensor 222 extends inwards from mounting point 220 by way of a radial extender. Both the gimbal arms and radial extender are driven by motors.

Pivot point 230 pivotably connects outer gimbal arm 214 to the fixed, headrest plinth portion of assembly 200. Stepper motor 234 precisely rotates outer gimbal arm 214 around pivot point 230 to a specified longitude around the patient's head.

Pivot point 232 and pivot point 233 pivotably connect inner gimbal arm 216 to outer gimbal arm 214. Stepper motor 236 precisely rotates inner gimbal arm around pivot points 232 and 233 to a specified latitude up and down the patient's head.

Stepper motor 238 pulls a cable, which threads through pulleys, some of which are shown as pulleys 246, to extend or retract radial extender. There may be one or more pulley and cable systems. In the exemplary embodiment, one cable system with both a pull and push side allow the cable to remain taut without slack.

By remotely locating stepper motor 238 away from mounting point 220 that holds sensor 222, the ferrous and nonferrous metals within the motor are kept away from the sensor. This minimizes or otherwise avoids potential electromagnetic interference (EMI) between an otherwise close motor and sensor.

While stepper motors are used in the exemplary embodiments, other types of motors, with encoders or other precision measuring means, may be used. It has been found that stepper motors with stop or limit switches perform well to accurately and precisely position gimbals at the resolutions required to acquire for patient data.

Figure 3A:
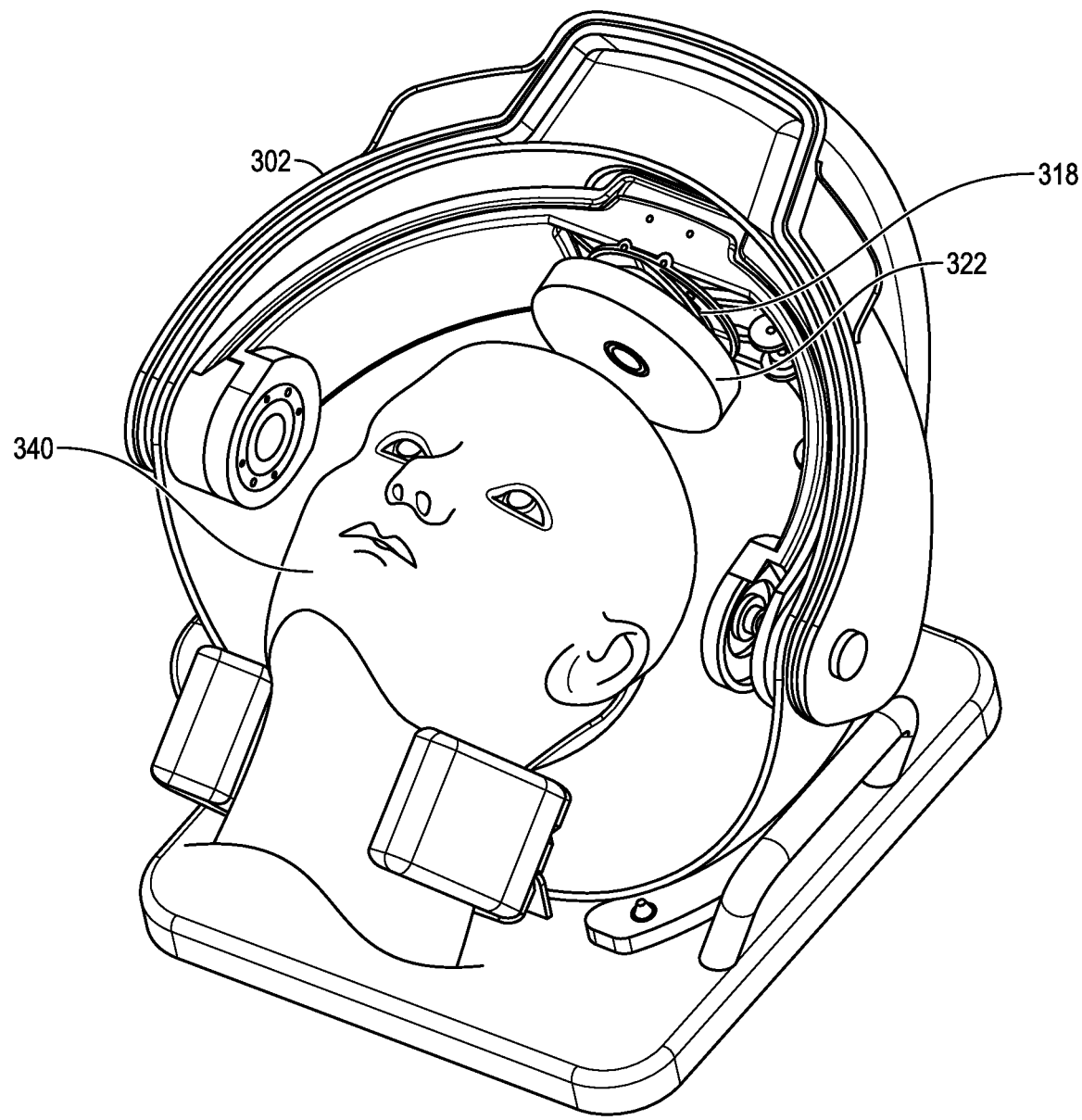
FIG. 3A illustrates a human subject in a device in accordance with an embodiment.
Figure 3B:
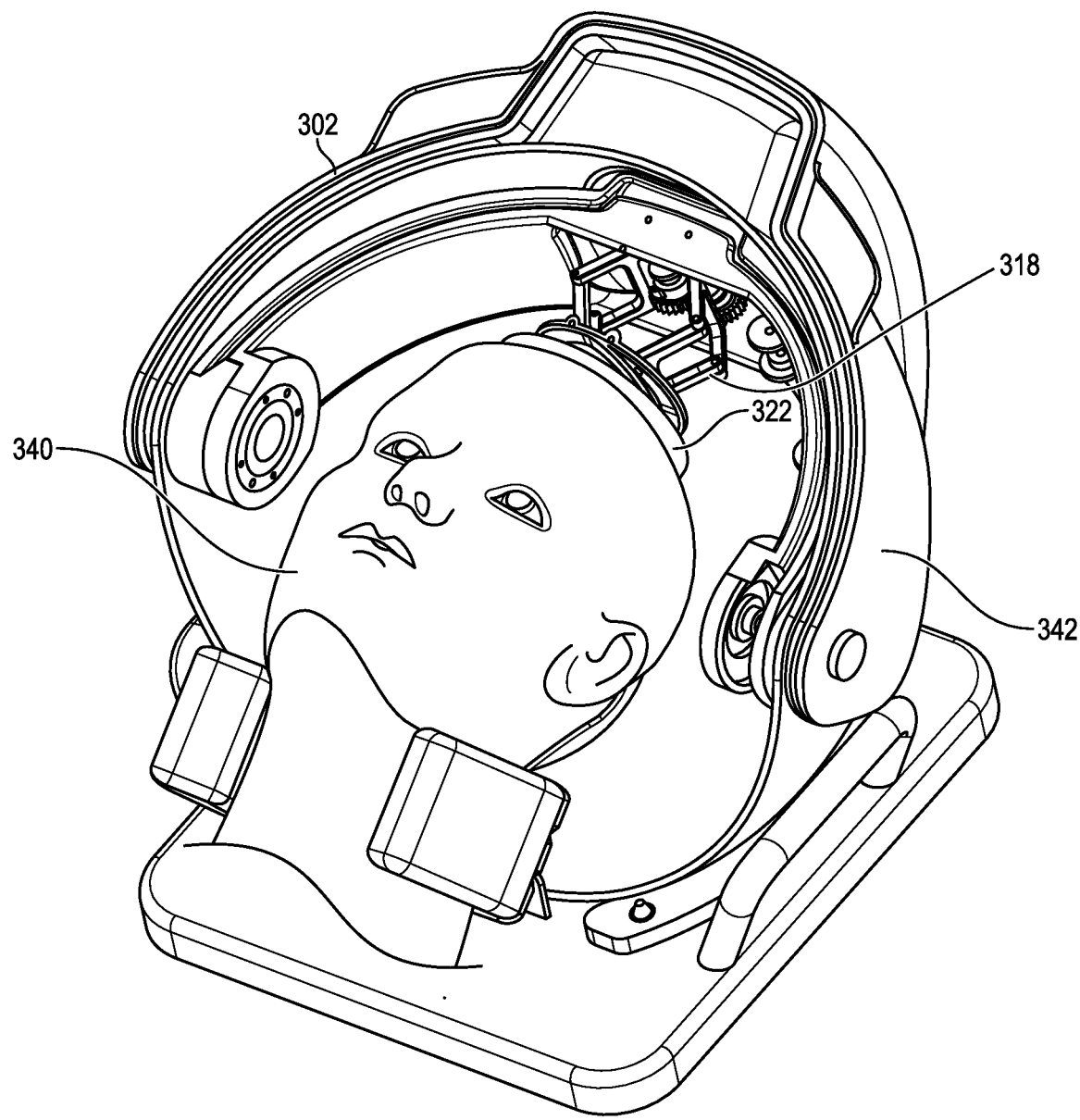
FIG. 3B illustrates a coil sensor radially extended to the subject's scalp of FIG. 3A.
Figure 3C:
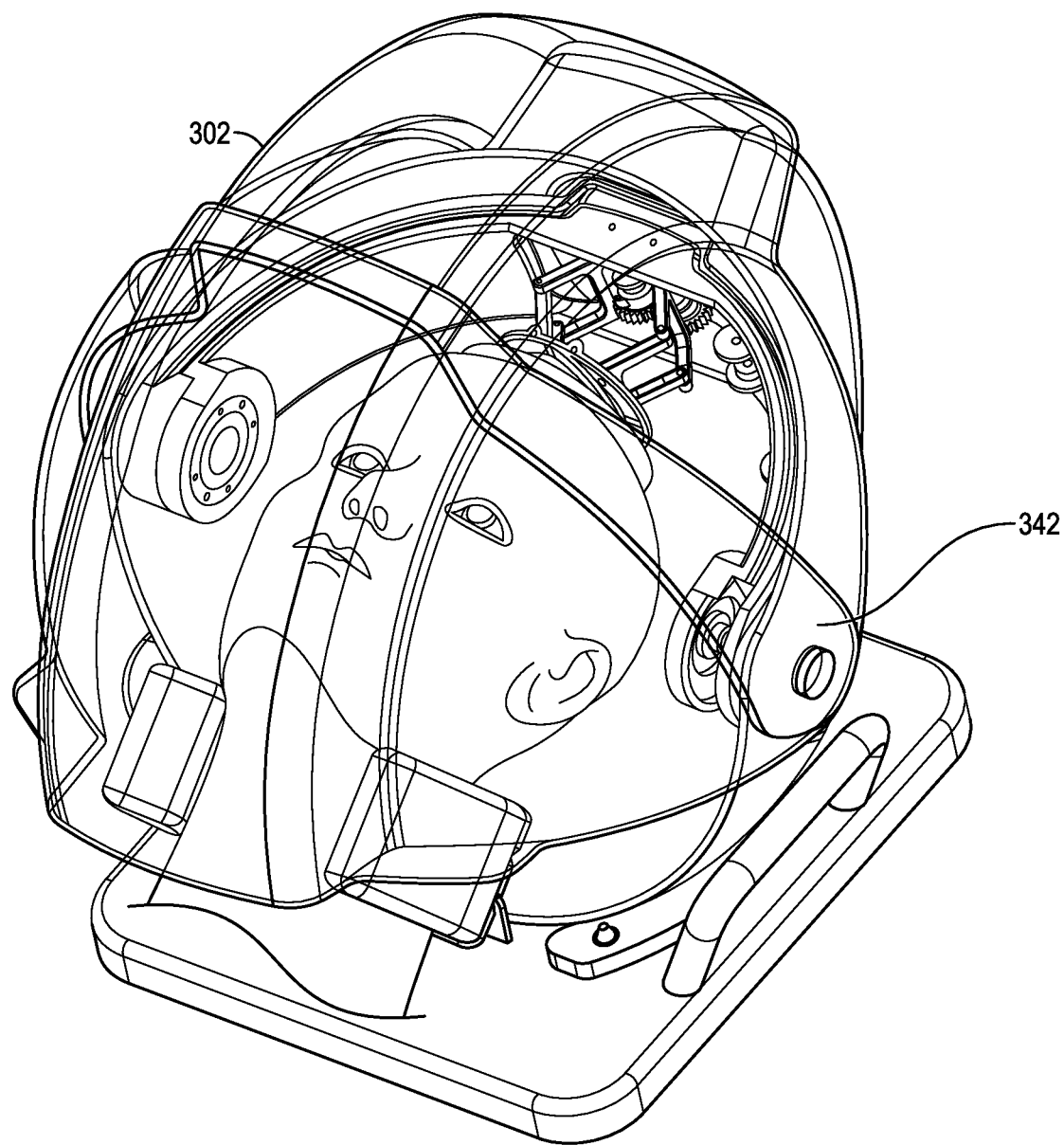
FIG. 3C is a perspective view of a face shield extended over the device of FIG. 3B.

FIGS. 3A-3C illustrates human head 340 undergoing medical diagnostics in device 302.

In FIG. 3A, radial extender 318 is retracted such that sensor 322 is away and well clear of head 340. In this retracted position, the gimbal armature may be freely swiveled around the head without mechanical interference.

In FIG. 3B, radial extender 318 is extended such that sensor 322 is pressed gently against head 340. Radial extender 318 is of the scissoring type, with legs that swing out from one another when opened and bypass each other when closed.

In this extended position, sensor 322 may slightly cant from its otherwise standard orientation that is normal to the radial line projecting from the notional center of the head. Compensating for the cant is discussed infra.

In some situations with the sensor extended, it may be beneficial to rotate the gimbal armature in latitude, longitude, or both directions in order to drag the sensor gently along the topology of the cranium. This may be to perform rapid scans in emergencies, make continuous measurements in space, or for pre- or post-calibration of instruments. Otherwise, the sensor may be retracted fully or partially before each gimbal movement to a different latitude and longitude.

Some scans may be more quickly, safely, or accurately accomplished if they can be done without interference by the patient him- or herself. FIG. 3B shows face shield 342 in a withdrawn position.

FIG. 3C is a perspective view of face shield 342 outwardly extended over the subject's head in device 302. Face shield 342 may help prevent willful or inadvertent interference with the sensor by the subject's hands and fingers. Unconscious patients often make wiping motions over their faces when something foreign touches their eyes, nose, or lips. Covering the head with a face shield may also prevent bedsheets, tubes, or wires in a hospital bed from interfering with an otherwise smooth scanning process, and it may serve as a reminder to stop others from reaching in while a scan is being performed. The gimbal thus may rotate through its scan points around the head unimpeded.

Figure 4:
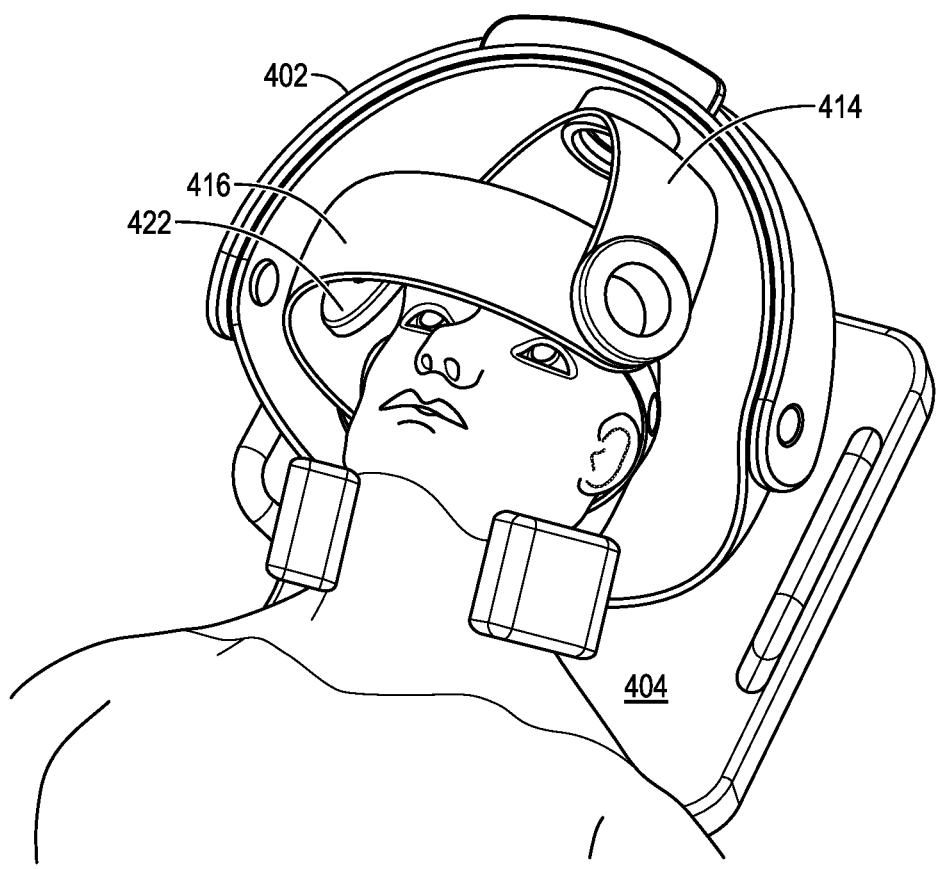
FIG. 4 illustrates a gimbal over the temple of a human subject in accordance with an embodiment.

FIG. 4 illustrates a gimbal over the temple of a human subject. The same may be part of a comprehensive scan or as a spot check of a region around the temple.

Gimbal arms 414 and 416 of device 402 are supported by headrest base 404 and have swiveled over the right temple of the subject's head. Sensor 422 is not yet extended to the patient's skin. The face shield is shown retracted for clarity.

This is part of a scan that may include a spot check of the temple in reaction to data from a computed tomography (CT) data or a magnetic resonance imaging (MRI) scan. Data from the CT or MRI can be uploaded to a computer system to automatically or manually determine one or more anatomical coordinates where further scans should take place.

For example, upon admission to a hospital, a patient may undergo a CT or MRI scan that discovers a lack of blood at particular 3D coordinates in the patient's brain. After blood thinners are administered, the same anatomical coordinates within the patient are monitored with the described device.

An "anatomical coordinate," "anatomical location," or "anatomical position" is a point, area, or volume on or within a body that remains relatively stationary with respect to organs and other features of the body, or as otherwise known in the art. The coordinate, location, or position may or may not be at a recognizable or a named part of the body, as it may be within the volume of an otherwise heterogenous organ. Analogs to an "anatomical" location are a geographic location or an absolute location.

Smart or adaptive scan patterns may be employed based on results of the CT, MRI, or previous scans by the device to maximize resolution over a particular anomaly and minimize scan time.

At the outset of care with a patient, however, a predetermined rote scan of measurements may be made over the head. These measurements, both of sensor cant angles when the sensor touches the head and of coil sensor electromagnetic readings, may be made with an eye towards establishing a basic cranial shape for reference points and an internal eddy current baseline. In some embodiments, a set number of discrete points, such as 64 discrete points, may be measured over the head. Or, the sensor may be slide over the head continuously in order to produce a more continuous, analog set of measurements.

Figure 5A:
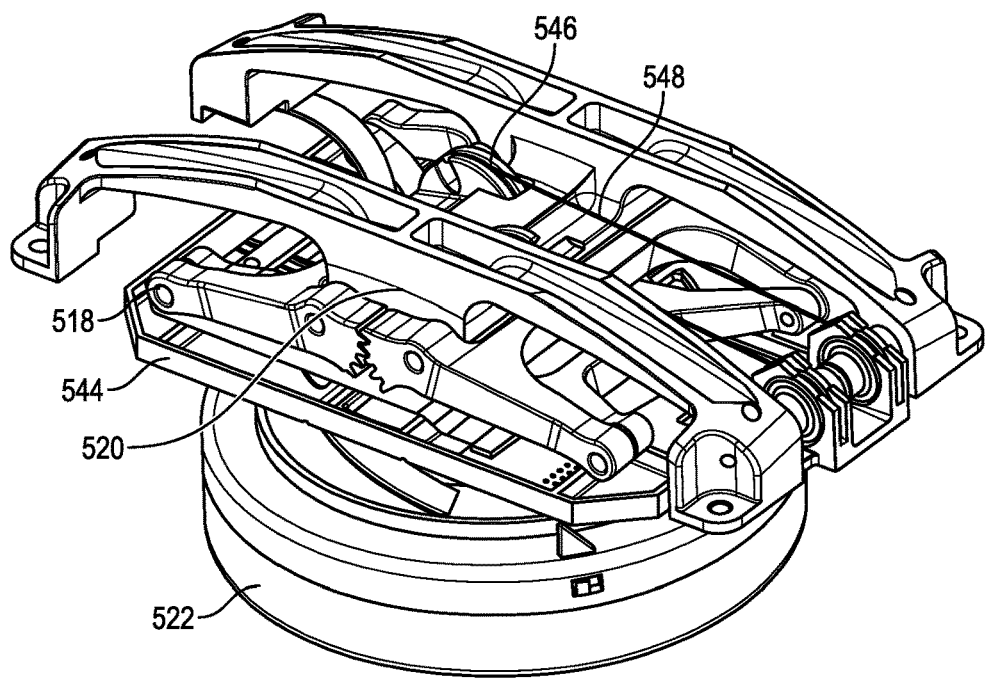
FIG. 5A is a perspective top and side view of a radial extender retracted in accordance with an embodiment.
Figure 5B:
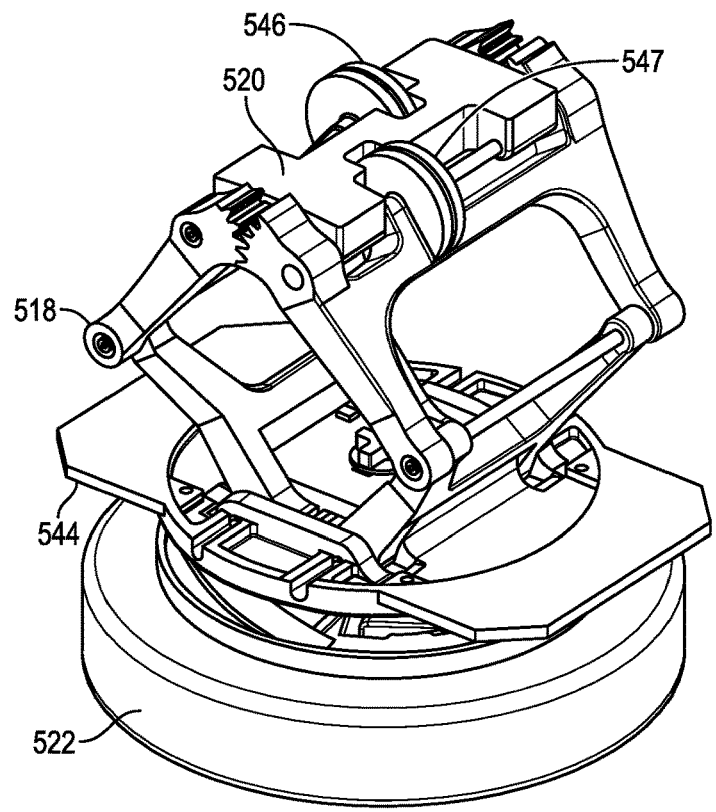
FIG. 5B illustrates the radial extender of FIG. 5A extended in accordance with an embodiment.

FIGS. 5A-5B illustrate radial extender 518 in two positions: unextended and extending end effector 544 and sensor 522 downward from mounting point 520.

In FIG. 5A, a scissoring mechanism is retracted with nesting legs folded within one another. Pulley wheel 546 is fixed to a force transmission shaft shared with partial gears. When cable 548 is pulled through pulley wheel 546 by a motor, pulley wheel 546 rotates the partial gears with respect to each other to extend the scissoring mechanism. The rotation continues until a limit switch is toggled.

In FIG. 5B, the scissoring mechanism is mostly extended. Another pulley wheel 547 is shown, this one being for retraction. When pulley wheel 547 is rotated by a second cable (not shown), it causes the partial gears to turn in the other direction, retracting end effector 544 toward mounting point 520. The cable may also have an end attached to the end effector in order to pull the end effector toward the mounting point.

Besides scissoring mechanisms, telescoping and other mechanical devices can be used to extend and retract the sensor. A motor may be collocated within the radial extender or may, like the exemplary embodiments shown, be remotely located.

Figure 6:
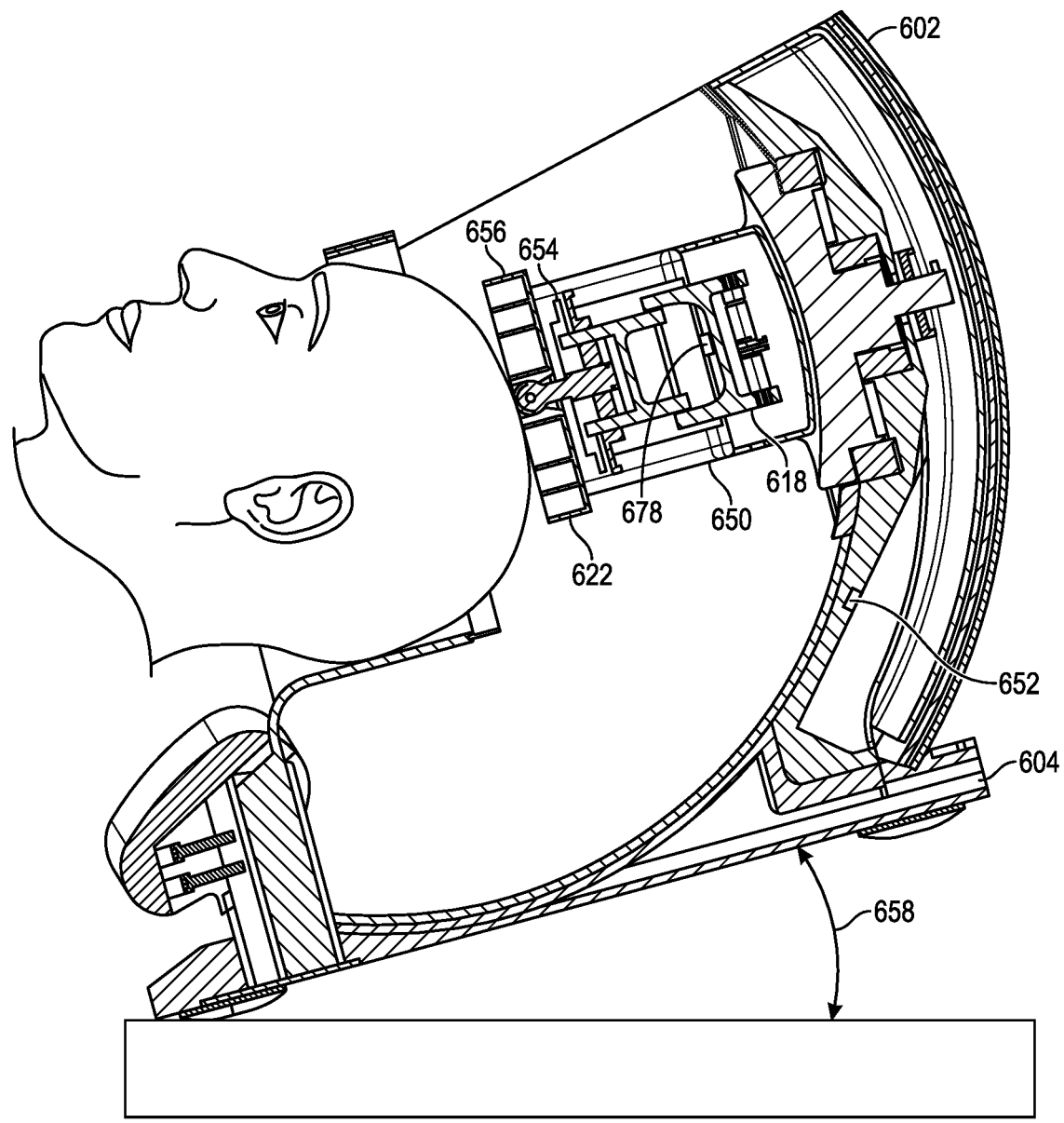
FIG. 6 is a vertical cross section view of a medical diagnostic device in accordance with an embodiment.

FIG. 6 is a vertical cross section view of a medical diagnostic device 602 with telescoping radial extender 650. Radial extender 650 is shown extended such that sensor 622 touches the top of a small subject's head. Radial extender 650 can move to the outer extreme as shown or be retracted to limit switch 678.

Three-dimensional (3D) accelerometer 652 is rigidly affixed to headrest plinth 604 and effectively measures inclination angle 658 between the nominal base and a flat table by detecting the gravitational vector. The inclination may be due to bed angle, bedding, supportive cushions, or other items. Accelerometer 652 outputs x-y-z components of acceleration due to gravity. The orientation of the gravitational vector gives the absolute orientation in space of the accelerometer 652.

If measurements from accelerometer 652 suddenly change, that may indicate that someone or something has bumped the table or bed, or otherwise moved the device, during a scan of measurements. A movement artifact in the accelerometer data may indicate that rescanning or compensating the data is necessary.

Another accelerometer pack, 3D accelerometer 654 is mounted at the end effector of radial extender 618. This accelerometer pack can provide deflection data at the end of the radial extender for calibration or otherwise.

Accelerometer 656 is rigidly affixed to sensor 622. Comparing the x-y-z components of acceleration due to gravity in accelerometer 656 with respect to those of accelerometer 652 enables the calculation of an orientation of sensor 622 with respect to headrest plinth 604. The orientation can be used to determine a sensor direction with respect to the headrest and thus the cranium itself. The sensor direction is evaluated to determine a precise anatomical location of where the sensor is pointed within the patient's brain.

Although accelerometers are shown for the tilt gauges, other sensors may be used to indicate tilt, including those employing plumb weights, a spirit level air bubble, or other tools.

Successive sensor orientations taken around the scalp can be used to automatically create a topological map of the cranium. This may provide a "sanity check" to see that the sensor's tilt gauges are performing precisely and/or accurately.

An initial scan can be performed to pre-map head locations. And a post-scan map can be performed as well. As the sensor is held at each location during the mapping, sensor recordings at all positions may be taken as well during each scan. These scans may enable compensation of movement by the patient or device during treatment.

Figure 7:
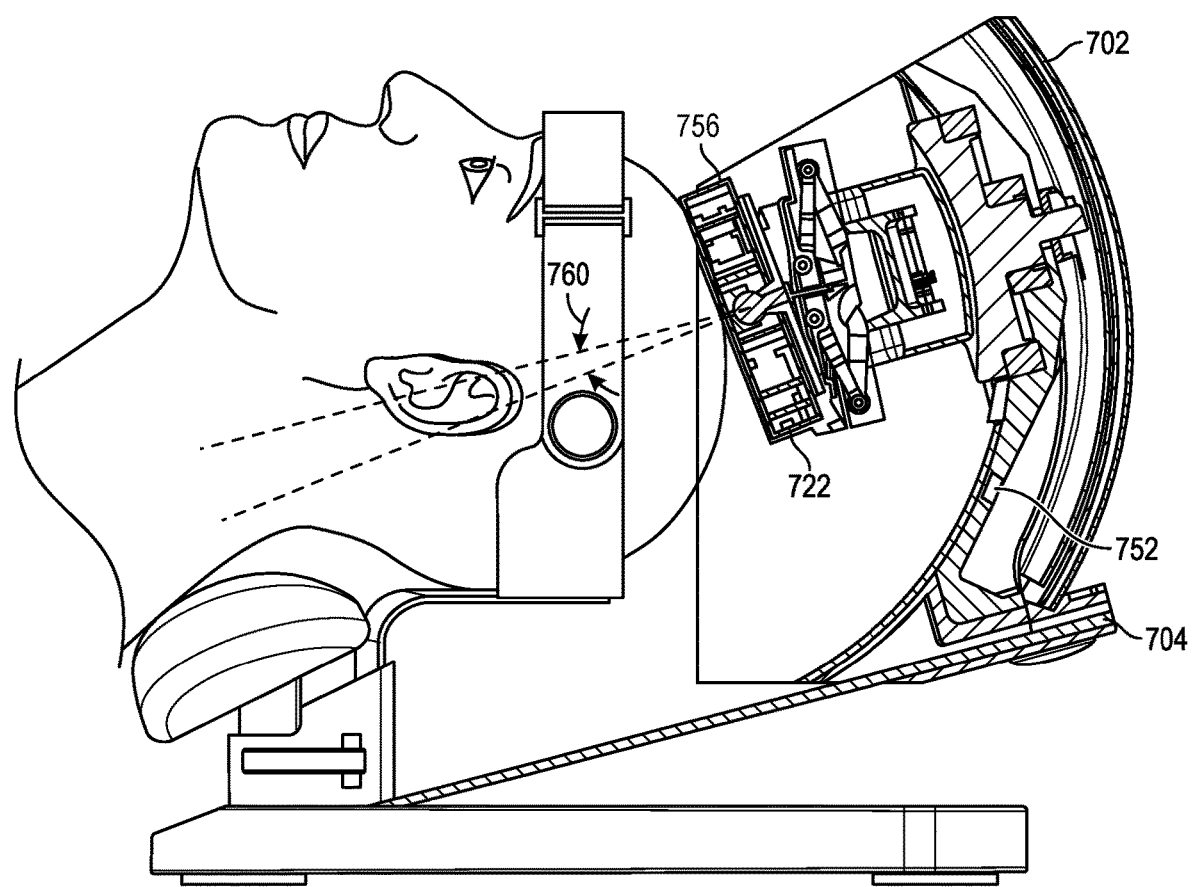
FIG. 7 is a vertical cross section view of a device showing an off-nominal tilt of a directional coil sensor in accordance with an embodiment.

FIG. 7 is a vertical cross section view of medical diagnostic device 702 showing an off-nominal tilt, or cant, of coil sensor 722. Base tilt gauge 752 is affixed to headrest plinth 704, which, through gimbal armature and a radial extender, supports coil sensor 722. Tilt gauge 756 is affixed to sensor 722 and indicates its orientation with respect to gravity.

Comparing the tilt angles with respect to gravity of tilt gauges 756 and 752, a 3D anatomical location of each measured value from the coil sensor is calculated. That is, even though sensor 756 is pointing at angle 760 off from its nominal, radial direction with respect to a notional center point within the cranium, the system can determine that an eddy current measurement is anterior (in the head) to where it would otherwise have taken place. The measured value from the coil, such as a frequency measurement or resistance measurement, can be appropriately adjusted based on the orientation.

FIGS. 8A-9B show screen renderings of lateral and ventral views of brain 862 within subject's head 860.

FIGS. 8A-8B show rendering 800A of lateral view of the brain and rendering 800B of ventral view of the brain, respectively. Area of increased conductivity 864 is shown centered between the left and right hemispheres in the Occipital lobe. The increased conductivity is likely caused by a pool of blood, indicating a hemorrhagic stroke.

FIGS. 9A-9B shown rendering 900A of lateral view of the brain and rendering 900B of ventral view of the brain, respectively. These are taken at a later time than those of FIGS. 8A-8B. Area of increased conductivity 964 is in the same anatomical location within the brain as that of area 864—but is larger in volume. This bears the hallmark of a worsening hemorrhagic stroke. This is seen in both the lateral and ventral views.

The increased blood pooling due to this data may prompt emergency intervention with the patient to drain the blood or at least relieve pressure that may be building within the brain.

With an eddy current coil sensor, determining baseline conductivities throughout the brain may be important at the start of treatment. Then, like as shown here, the conductivities may change over time, and those changes and anatomical locations may be flagged or otherwise indicated to treating personnel.

Another way of using an eddy current coil sensor is to compare readings from anatomical positions exactly opposite each other in the left and right hemispheres of the brain. If the readings are essentially the same, then it may indicate that both sides are healthy. However, if measured values are substantially different between the left and right hemispheres, it may indicate blood pooling (hemorrhagic), or a lack of blood (ischemic), in either of the regions. Such a finding may prompt further diagnostics, such as a CT or MRI scan.

Figure 10:
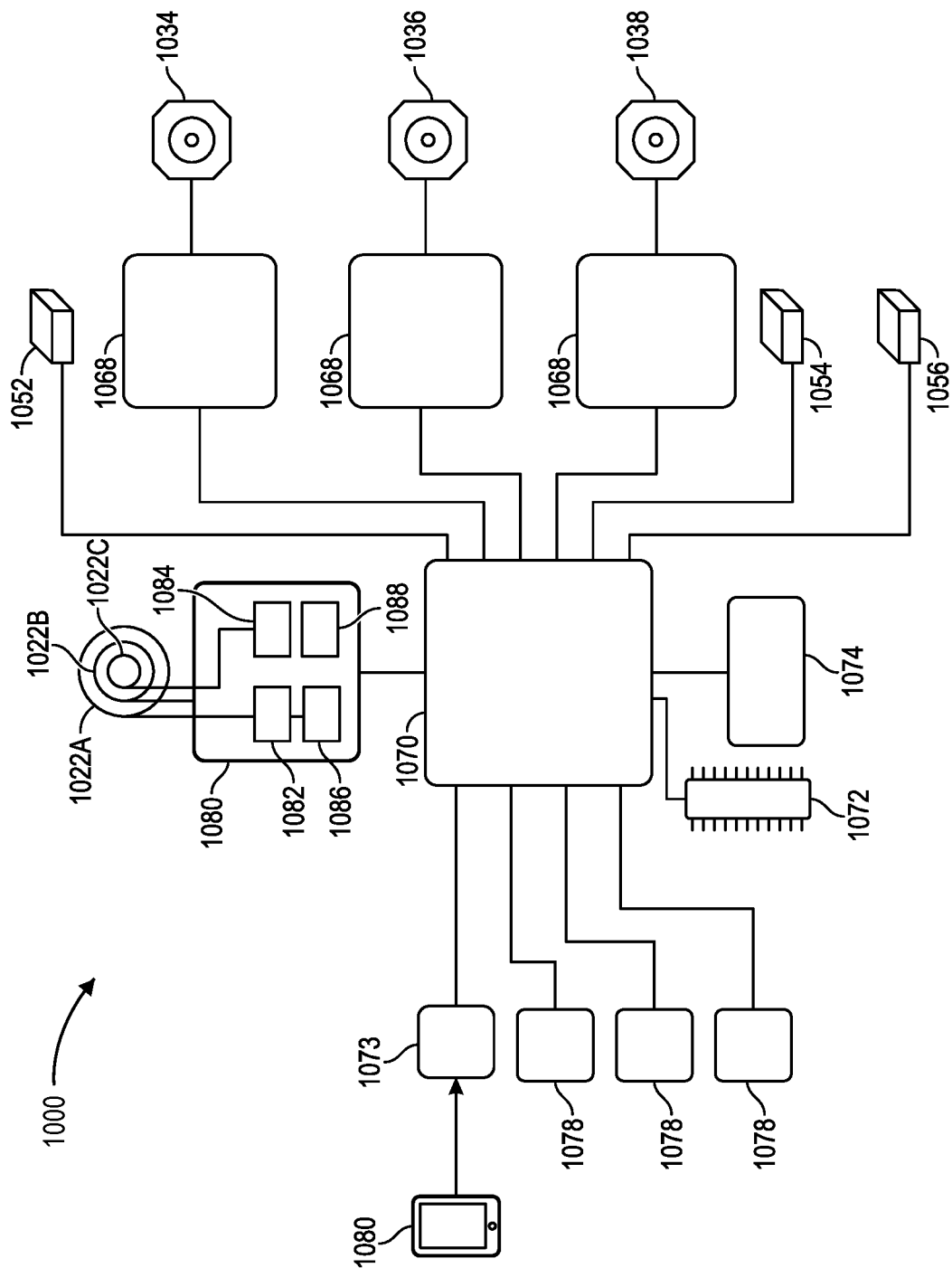
FIG. 10 is a connection diagram for a gimbal control system in accordance with an embodiment.

FIG. 10 illustrates gimbal control system 1000, which is controlled by a tablet device or personal computer (PC) 1080.

Computer processor microcontroller 1070 processes machine instructions and data from machine-readable non-transitory memory 1072. Memory 1072 includes instructions, such as programming language, to cause microcontroller 1070 to command gimbal and radial extender movement through motor drivers 1068, energize the coil through coil sensor driver 1080, read accelerometers 1052, 1054, and 1056, process data, and indicate functions and measurements through screens, light emitting diodes (LEDs) 1074, audio, or other output devices.

Microcontroller 1070 energizes first resistive, inductive, and capacitive (RLC) circuit 1082, which is connected with first frequency counter 1086. The first RLC circuit is connected with outer coil 1022A. Measured values, based on outputs from frequency counter 1086, are generated for the large coil. Microcontroller 1070 also energizes another resistive RLC circuit 1084, which is connected with another frequency counter 1088. This second RLC circuit is connected with inner coil 1022C. For succinctness, coil 1022B's circuit is not shown. Measured values, based on outputs from frequency counter 1088, are generated for the small coil.

Motors 1034, 1036, and 1038 are controlled through their respective motor drivers 1068 by microcontroller 1070.

Computer hardware systems suitable for implementing or controlling the microcontroller include personal computer (PC), front- or backend set of servers, or other types of computer systems. The computer system can include a central processing unit (CPU) for running software applications and optionally an operating system. The CPU may be made up of one or more homogeneous or heterogeneous processing cores. Memory can store applications and data for use by the CPU. Storage can provide non-volatile storage and other computer readable media for applications and data and may include fixed disk drives, removable disk drives, flash memory devices, and CD-ROM, DVD-ROM, BLU-RAY, HD-DVD, or other optical storage devices, as well as signal transmission and storage media. User input devices can communicate user inputs from one or more users to the computer system examples of which may include keyboards, mice, joysticks, touch pads, touch screens, still or video cameras, and/or microphones. A network interface can allow the computer system to communicate with other computer systems via an electronic communications network, and may include wired or wireless communication over local area networks and wide area networks such as the Internet. An audio processor can be adapted to generate analog or digital audio output from instructions and/or data provided by the CPU, memory, and/or storage. The components of the computer system, including the CPU, memory, data storage, user input devices, network interface, and audio processor can be connected via one or more data buses.

A graphics subsystem can be connected with the data bus and the components of the computer system. The graphics subsystem can include a graphics processing unit (GPU) and graphics memory. The graphics memory can include a display memory (e.g., a frame buffer) used for storing pixel data for each pixel of an output image. The graphics memory can be integrated in the same device as the GPU, connected as a separate device with the GPU, and/or implemented within the memory. Pixel data can be provided to the graphics memory directly from the CPU. Alternatively, the CPU can provide the GPU with data and/or instructions defining the desired output images, from which the GPU can generate the pixel data of one or more output images. The data and/or instructions defining the desired output images can be stored in the memory and/or graphics memory. In an embodiment, the GPU can include 3D rendering capabilities for generating pixel data for output images from instructions and data defining the geometry, lighting, shading, texturing, motion, and/or camera parameters for a scene. The GPU can further include one or more programmable execution units capable of executing shader programs.

The graphics subsystem can periodically output pixel data for an image from the graphics memory to be displayed on the display device. The display device can be any device capable of displaying visual information in response to a signal from the computer system, including cathode ray tube (CRT), liquid crystal display (LCD), plasma, and organic light emitting diode (OLED) displays. The computer system can provide the display device with an analog or digital signal.

In accordance with various embodiments, the CPU can be one or more general purpose microprocessors having one or more processing cores. Further embodiments can be implemented using one or more CPUs with microprocessor architectures specifically adapted for highly parallel and computationally intensive applications, such as media and interactive entertainment applications.

The components of a system may be connected via a network, which may be any combination of the following: the Internet, an internet protocol (IP) network, an intranet, a wide-area network (WAN), a local-area network (LAN), a virtual private network (VPN), the Public Switched Telephone Network (PSTN), or any other type of network supporting data communication between devices described herein, in different embodiments. A network may include both wired and wireless connections, including optical links. Many other examples are possible and apparent to those skilled in the art in light of this disclosure. In the discussion herein, a network may or may not be noted specifically.

Figure 11:
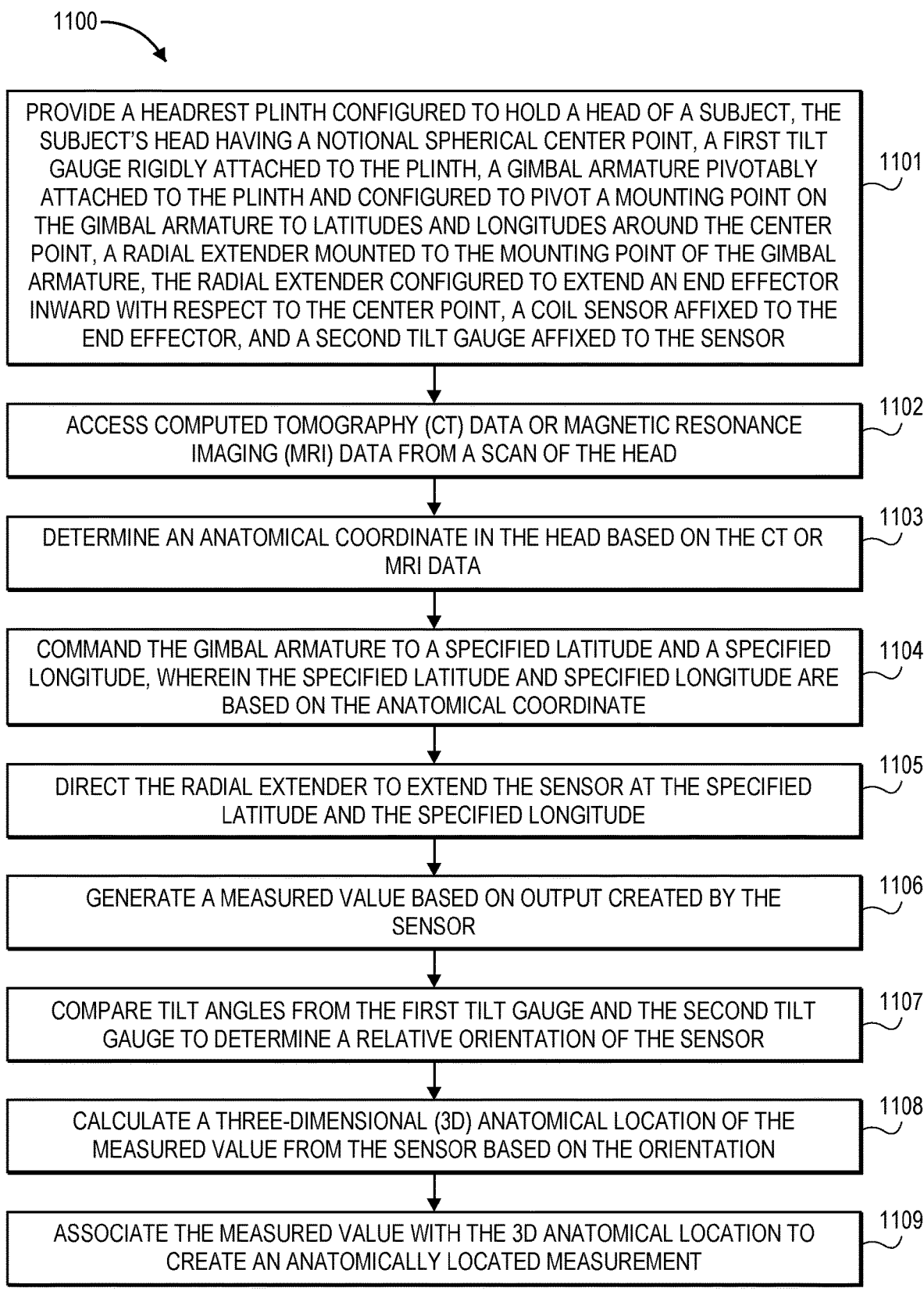
FIG. 11 is a flowchart illustrating a process in accordance with an embodiment.

FIG. 11 is a flowchart illustrating process 1100 in accordance with an embodiment. In operation 1101, a headrest plinth configured to hold a head of a subject is provided, the subject's head having a notional spherical center point. A first tilt gauge rigidly attached to the plinth, a gimbal armature pivotably attached to the plinth and configured to pivot a mounting point on the gimbal armature to latitudes and longitudes around the center point, a radial extender configured to extend an end effector inward with respect to the center point, a coil sensor affixed to the end effector, and a second tilt gauge affixed to the coil sensor are provided as well. In operation 1102, computed tomography (CT) data or magnetic resonance imaging (MRI) data from a scan of the head is received, read, or otherwise accessed. In operation 1103, an anatomical coordinate in the head is determined based on the CT or MRI data. In operation 1104, the gimbal armature is commanded to a specified latitude and a specified longitude, wherein the specified latitude and the specified longitude are based on the anatomical coordinate. In operation 1105, the radial extender is directed to extend the sensor at the specified latitude and the specified longitude. In operation 1106, a measured value is generated based on an output created by the sensor. In operation 1107, tilt angles from the first tilt gauge and the second tilt gauge are compared in order to determine a relative orientation of the sensor. In operation 1108, a three-dimensional (3D) anatomical location of the measured value from the sensor is calculated based on the relative orientation. In operation 1109, the measured value is associated with the 3D anatomical location to create an anatomically located measurement.

Figure 12:
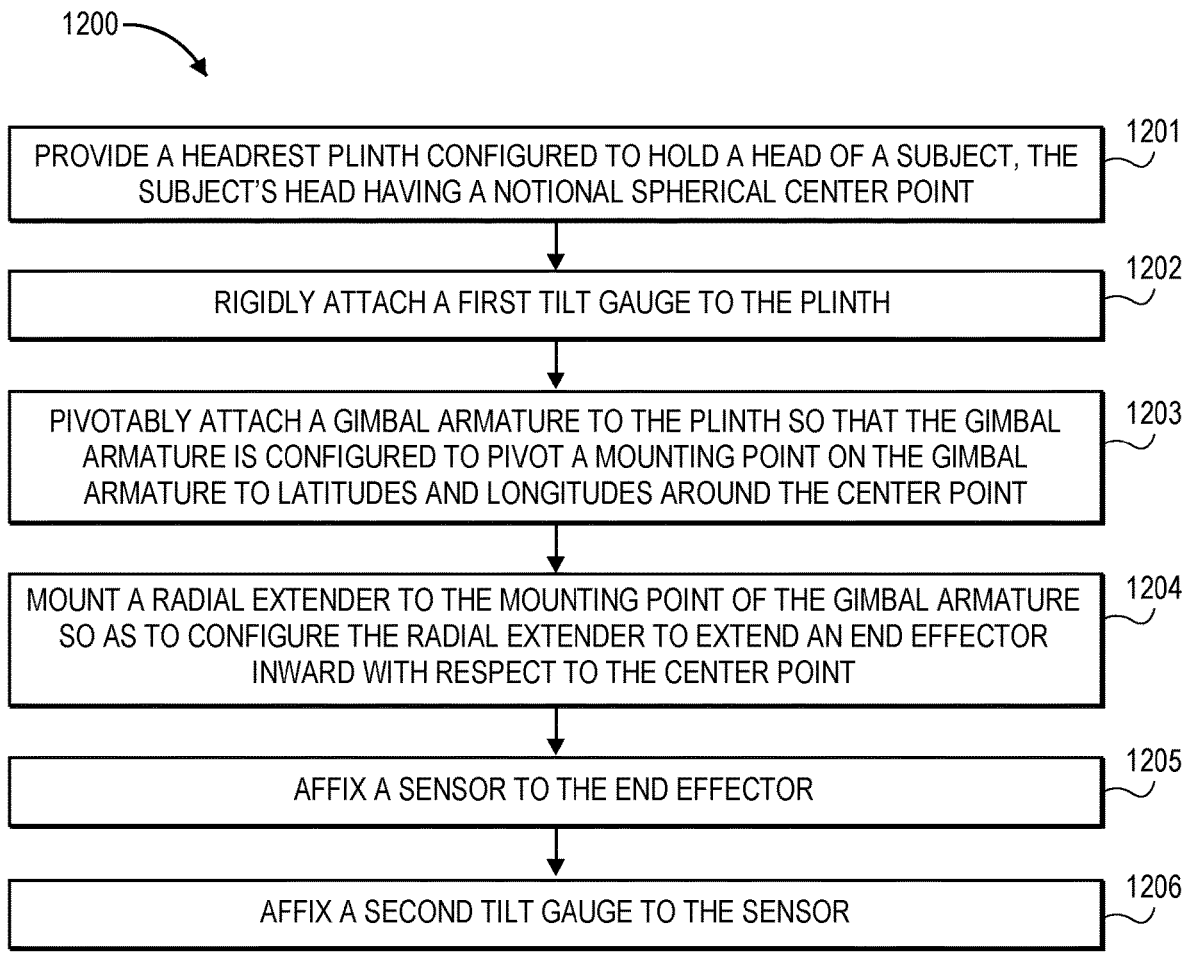
FIG. 12 is a flowchart illustrating a process in accordance with an embodiment.

FIG. 12 is a flowchart illustrating process 1200 in accordance with an embodiment. In operation 1201, a headrest plinth configured to hold a head of a subject, the subject's head having a notional spherical center point, is provided. In operation 1202, a first tilt gauge is rigidly attached to the plinth. In operation 1203, a gimbal armature is pivotably attached to the plinth so that the gimbal armature is configured to pivot a mounting point on the gimbal armature to latitudes and longitudes around the center point. In operation 1204, a radial extender is mounted to the mounting point of the gimbal armature so as to configure the radial extender to extend an end effector inward with respect to the center point. In operation 1205, a coil sensor is affixed to the end effector. In operation 1206, a second tilt gauge is affixed to the sensor.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within +1%, +2%, +5%, +10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. An inductive sensor apparatus for brain diagnostics, the apparatus comprising:
    a headrest plinth configured to hold a head of a subject, the subject's head having a notional spherical center point;
    a first tilt gauge rigidly attached to the plinth;
    a gimbal armature pivotably attached to the plinth and configured to pivot a mounting point on the gimbal armature to latitudes and longitudes around the center point;
    a radial extender mounted to the mounting point of the gimbal armature, the radial extender configured to extend an end effector inward with respect to the center point;
    a coil sensor affixed to the end effector;
    a second tilt gauge affixed to the coil sensor;
    a resistive, inductive, and capacitive (RLC) circuit electrically connected with the coil sensor; and
    a frequency counter electrically connected with the RLC circuit.

2. The apparatus of claim 1 further comprising:
    a memory; and
    a computer processor operatively coupled with a machine-readable non-transitory medium embodying information indicative of instructions for causing the computer processor to perform operations comprising:
        comparing tilt angles from the first tilt gauge and the second tilt gauge to determine a relative orientation of the coil sensor; and
        calculating a three-dimensional (3D) anatomical location of a measured value from the coil sensor based on the orientation.

3. The apparatus of claim 2 wherein the operations further comprise:
    adjusting a measured value from the coil sensor based on the orientation.

4. The apparatus of claim 3 wherein the adjusting includes compensating for movement of the subject's head between measurements at the same anatomical location.

5. The apparatus of claim 2 wherein the operations further comprise:
    commanding the gimbal armature to rotate to a specified latitude and a specified longitude;
    directing the radial extender to extend the coil sensor at the specified latitude and the specified longitude;
    generating a measured value based on output created by the coil sensor; and
    associating the measured value with the 3D anatomical location to create an anatomically located measurement.

6. The apparatus of claim 5 wherein the anatomically located measurement is from a left hemisphere of the head, the operations further comprising:
    making an anatomically located measurement on a right hemisphere of the head;
    comparing the measurements from the left and right hemispheres of the head; and
    outputting an indication based on the comparing.

7. The apparatus of claim 5 wherein the anatomically located measurement is from an earlier time, the operations further comprising:
    making an anatomically located measurement at a later time;

comparing the measurements from the earlier and later times; and outputting an indication based on the comparing.

8. The apparatus of claim 5 wherein the operations further comprise:
accessing computed tomography (CT) data or magnetic resonance imaging (MRI) data from a scan of the head; and
determining an anatomical coordinate in the head based on the CT or MRI data,
wherein the specified latitude and specified longitude are based on the anatomical coordinate.

9. The apparatus of claim 5 wherein the operations further comprise:
creating a set of anatomically located measurements that includes the anatomically located measurement; and
generating a physical topography of the head from the measurements or rendering an image based on the measurements.

10. The apparatus of claim 2 wherein the operations further comprise:
generating measured values based on outputs from the frequency counter when the coil sensor is at a cranial location on the head.

11. The apparatus of claim 10 wherein the coil sensor is a first coil sensor, the RLC circuit is a first RLC circuit, and the frequency counter is a first frequency counter, the apparatus further comprising:
a second coil sensor having a larger or smaller diameter than the first coil sensor, the first and second coil sensors sharing a housing;
a second RLC circuit electrically connected with the second coil sensor; and
a second frequency counter electrically connected with the second RLC circuit.

12. The apparatus of claim 1 wherein the first and second tilt gauges include three-dimensional (3D) accelerometers.

13. The apparatus of claim 1 wherein the radial extender includes a scissoring device or a telescoping mechanism.

14. The apparatus of claim 1 further comprising:
a motor;
a pulley wheel on the mounting point; and
a pulley cable extending between the motor and the radial extender through the pulley wheel,
the motor located remotely from the mounting point in order to avoid electromagnetic interference with the coil sensor.

15. A method of anatomically locating measurements in a subject's brain, the method comprising:
providing a headrest plinth configured to hold a head of a subject, the subject's head having a notional spherical center point, a first tilt gauge rigidly attached to the plinth, a gimbal armature pivotably attached to the plinth and configured to pivot a mounting point on the gimbal armature to latitudes and longitudes around the center point, a radial extender mounted to the mounting point of the gimbal armature, the radial extender configured to extend an end effector inward with respect to the center point, a coil sensor affixed to the end effector, a second tilt gauge affixed to the coil sensor, a resistive, inductive, and capacitive (RLC) circuit electrically connected with the coil sensor, and a frequency counter electrically connected with the RLC circuit;
comparing tilt angles from the first tilt gauge and the second tilt gauge to determine a relative orientation of the coil sensor; and
calculating a three-dimensional (3D) anatomical location of a measured value from the coil sensor based on the orientation.

16. The method of claim 15 further comprising:
adjusting a measured value from the coil sensor based on the orientation.

17. The method of claim 15 further comprising:
commanding the gimbal armature to a specified latitude and a specified longitude;
directing the radial extender to extend the coil sensor at the specified latitude and the specified longitude;
generating a measured value based on output created by the coil sensor; and
associating the measured value with the 3D anatomical location to create an anatomically located measurement.

18. The method of claim 17 wherein the anatomically located measurement is from a left hemisphere of the head, the method further comprising:
making an anatomically located measurement on a right hemisphere of the head;
comparing the measurements from the left and right hemispheres of the head; and
outputting an indication based on the comparing.

19. The method of claim 17 wherein the anatomically located measurement is from an earlier time, the method further comprising:
making an anatomically located measurement at a later time;
comparing the measurements from the earlier and later times; and
outputting an indication based on the comparing.

20. A method of manufacturing an inductive sensor apparatus for brain diagnostics, the method comprising:
providing a headrest plinth configured to hold a head of a subject, the subject's head having a notional spherical center point;
rigidly attaching a first tilt gauge to the plinth;
pivotably attaching a gimbal armature to the plinth so that the gimbal armature is configured to pivot a mounting point on the gimbal armature to latitudes and longitudes around the center point;
mounting a radial extender to the mounting point of the gimbal armature so as to configure the radial extender to extend an end effector inward with respect to the center point;
affixing a coil sensor to the end effector;
affixing a second tilt gauge to the coil sensor;
electrically connecting a resistive, inductive, and capacitive (RLC) circuit with the coil sensor; and
electrically connecting a frequency counter with the RLC circuit.

* * * * *